United States Patent
Stahl et al.

(10) Patent No.: US 7,576,195 B2
(45) Date of Patent: Aug. 18, 2009

(54) ENDOSPERM-SPECIFIC PLANT PROMOTER FOR CULTIVATED PLANTS

(75) Inventors: Rainer Stahl, Bonn (DE); Harald Dargatz, Andernach (DE); Renate Luhrs, Bonn (DE); Matthias Berkemeyer, Graz (AT)

(73) Assignee: Maltagen Forschung GmbH, Andernach (DE)

( * ) Notice: Subject to any disclaimer, the term of this patent is extended or adjusted under 35 U.S.C. 154(b) by 25 days.

(21) Appl. No.: 10/571,175

(22) PCT Filed: Sep. 2, 2004

(86) PCT No.: PCT/EP2004/009762

§ 371 (c)(1),
(2), (4) Date: Nov. 13, 2006

(87) PCT Pub. No.: WO2005/026366

PCT Pub. Date: Mar. 24, 2005

(65) Prior Publication Data

US 2007/0199106 A1 Aug. 23, 2007

(30) Foreign Application Priority Data

Sep. 11, 2003 (DE) ................. 103 43 326

(51) Int. Cl.
*C12N 15/63* (2006.01)
*C12N 5/14* (2006.01)
*C12N 15/82* (2006.01)
*C07H 21/04* (2006.01)
*A01H 5/00* (2006.01)

(52) U.S. Cl. ............... 536/24.1; 435/320.1; 435/468; 800/278; 800/295

(58) Field of Classification Search ............... None
See application file for complete search history.

(56) References Cited

OTHER PUBLICATIONS

Palenzuela et al. (Gene, 70:271-281, 1988; Applicant's IDS).*
Zhang et al. (EMBL, Sequence Accession No. CA002146, Published, Nov. 2, 2002, Applicant's IDS).*
Kim et al. (Plant Molecular Biology, 24:105-117, 1994).*
Donald et al. (EMBO J. 9:1717-1726, 1990).*
Benfey et al. (Science 250:959-966, 1990).*
Wells (Biochemistry, 29:8509-8517, 1990).*
Ngo et al. (The Protein Folding Problem and Tertiary Structure Prediction, K. Merz, and S. Le Grand (eds.) pp. 492-495, 1994).*
Guo et al. (PNAS, 101: 9205-9210, 2004.*
Keskin et al. (Protein Science, 13:1043-1055, 2004).*
Thornton et al. (Nature structural Biology, structural genomics supplement, Nov. 2000).*
Mendez, Enrique et al., "Primary structure and inhibitation of protein synthesis in eukaryotic cell-free system of a novel thionin, γ-hordothionin, from barley endosperm," *Eur. J. Biochem.*, 194, 533-539 (1990).
Rodriguez-Palenzuela, Pablo et al., "Nucleotide sequence and endosperm-specific expression of the structural gene for the toxin αhordothionin in barley," *Gene*, 70, 271-281 (1988).
Zhang, H. et al., "Barley ESTs from Germinating Seeds," Unpublished. (Database EMBL, Accession No. CA002146, Nov. 8, 2002).

* cited by examiner

*Primary Examiner*—Phuong T Bui
*Assistant Examiner*—Vinod Kumar
(74) *Attorney, Agent, or Firm*—Leydig, Voit & Mayer, Ltd.

(57) ABSTRACT

The invention provides an endosperm-specific plant promoter, as well as vectors, plant cells, and plant tissues comprising the endosperm-specific promoter. The invention also provides methods of using the endosperm-specific promoter.

23 Claims, 3 Drawing Sheets

SEQUENCE LISTING

<160> NUMBER OF SEQ ID NOS: 4

<210> SEQ ID NO 1
<211> LENGTH: 1564
<212> TYPE: DNA
<213> ORGANISM: Hordeum vulgare
<220> FEATURE:
<221> NAME/KEY: misc_feature
<222> LOCATION: (837)..(837)
<223> OTHER INFORMATION: n=c, t

<400> SEQUENCE: 1

```
gagctcggag gcggtcgtgc atggactgga agcagcatgc atgcatgcat gcatcgtggc      60
ggagaggctg gccgcgtggc gtgccgcgtg atcgatgtcg ttcacgtggc ggcctcggtg     120
catgcggcgc ccaggtatat acgcacgaga cagtgttcgc ctctggctgc ggcggtgcat     180
gcatgccagg ttgccagggc accgggcacg agagcgtttg gtagtcggcg ggcaggtagg     240
gcggccgccg aggtagtaga tctcggcgag ctgccctggg cgcgtggctc gtccacggcc     300
ggcctgggct tgcatgcagg acagcgcgcg ccaggcaagc tctgcccgcc ggtaggacca     360
cggatcgatc gagacttcga gagtgatccc agggtcaagt gcacgcacgc actcgtttag     420
acgatggaag atcgcctcgg ccggcctctg tcgggccaat acttcgatca gatggcatgc     480
atgcattttc atgtgggaac acatgtaatt tcgttcactg catgcttacc ttgttatcag     540
atctgtaaga ctgcttttc tgaagattgt cagcaagttt ttgtctggct tgcaatgcgg      600
catcgatgtt gcacttcaga acaactttga ccgatcccct attcgaccgt aaggaaggat     660
aaattcggtt ttcttacctt acaccacgtc tagtcgatcc cctaaacata ttacacaagt     720
aaaattatct tccatcgtcg aaaacacact tcaatctttg ctttctaaat acgctcatcc     780
cgcgcgcgcc cctccttctc ccacgtgttt aaatcaaata ttttatgat atactcnctc     840 cgttcttaaa tataagtctt taaagaggtt tcactagtgt actatatacg gatgtatata     900
gatttgtaga ttcactcatt ttgtttcgta tatagactcc tagtgaaata tcttaaaaga     960
cttatattta agaacggagg aagtatattg catagtgttt gaaattcatg cggctagaaa    1020
ataatgttta cacagtttca attttgttca actaatataa agatactttt ttaaataaga    1080
gcatataaag acatcattga aggagtaaaa aaaatctaca ctaactttac ttcgttgaat    1140
cctcttaact tttaaaggat tggattggat tggatagagt tgaaacgggc ggatcgatcg    1200
gctcgagcgg cgcagccttc cgagacctcc atgtacgtat agacccttt tgcgaccagg    1260 cacttgacag tttcgagacc atcgatcatc tcgtagtcca acgcccttc gtcacaactc    1320 acaagagaac ttcggttcaa attcttgcgt ccaaagggc gactcctctc gtcccaaagc    1380
atccagacgc acgctgagtt ggaacaagca gctgaacaac acggccttcc agcccgacag    1440
gtggcgacgc tacatgcagg atgcctgcca cgaacgcacc tgcatgcaag cacggcagcg    1500
tcctcctccg gcccaaaccc cctatataag tagagagctt ctcttcctgg caacaacaac    1560
```

```
aaca                                                              1564

<210> SEQ ID NO 2
<211> LENGTH: 208
<212> TYPE: DNA
<213> ORGANISM: Hordeum vulgare

<400> SEQUENCE: 2
atggagttca agacgaaggc gaccgtgtgc gcggcgctgc tggtgctgct cctgctttcg      60
tcctgtacgt aattaagccc gaacgggcgc tcccaaactt attatgattt gctgctgctt     120
attgttatgg tctaacgctt gtggccggcc accgggacat gttttttcag acgacggcgg     180
cgacggcggc gtcggcgtgg cggaggcg                                       208

<210> SEQ ID NO 3
<211> LENGTH: 106
<212> TYPE: DNA
<213> ORGANISM: Hordeum vulgare

<400> SEQUENCE: 3
gtacgtaatt aagcccgaac gggcgctccc aaacttatta tgatttgctg ctgcttattg      60
ttatggtcta acgcttgtgg ccggccaccg ggacatgttt tttcag                    106

<210> SEQ ID NO 4
<211> LENGTH: 1850
<212> TYPE: DNA
<213> ORGANISM: Hordeum vulgare
<220> FEATURE:
<221> NAME/KEY: misc_feature
<222> LOCATION: (837)..(837)
<223> OTHER INFORMATION: n=c, t

<400> SEQUENCE: 4
gagctcggag gcggtcgtgc atggactgga agcagcatgc atgcatgcat gcatcgtggc      60
ggagaggctg gccgcgtggc gtgccgcgtg atcgatgtcg ttcacgtggc ggcctcggtg     120
catgcggcgc ccaggtatat acgcacgaga cagtgttcgc ctctggctgc ggcggtgcat     180
gcatgccagg ttgccagggc accgggcacg agagcgtttg gtagtcggcg ggcaggtagg     240
gcggccgccg aggtagtaga tctcggcgag ctgccctggg cgcgtggctc gtccacggcc     300
ggcctgggct tgcatgcagg acagcgcgcg ccaggcaagc tctgcccgcc ggtaggacca     360
cggatcgatc gagacttcga gagtgatccc agggtcaagt gcacgcacgc actcgtttag     420
acgatggaag atcgcctcgg ccggcctctg tcgggccaat acttcgatca gatggcatgc     480
atgcattttc atgtgggaac acatgtaatt tcgttcactg catgcttacc ttgttatcag     540
atctgtaaga ctgcttttc tgaagattgt cagcaagttt ttgtctggct tgcaatgcgg     600
catcgatgtt gcacttcaga acaactttga ccgatcccct attcgaccgt aaggaaggat     660
aaattcggtt ttcttacctt acaccacgtc tagtcgatcc cctaaacata ttacacaagt     720
aaaattatct tccatcgtcg aaaacacact tcaatctttg ctttctaaat acgctcatcc     780
cgcgcgcgcc cctccttctc ccacgtgttt aaatcaaata ttttttatgat atactcnctc     840 cgttccttaaa tataagtctt taagagggtt tcactagtgt actatatacg gatgtatata     900
gatttgtaga ttcactcatt tgtttcgta tatagactcc tagtgaaata tcttaaaaga     960 cttatatttta agaacggagg aagtatattg catagtgttt gaaattcatg cggctagaaa    1020 ataatgtttta cacagtttca attttgttca actaatataa agatacttttt ttaaataaga    1080
```

-continued

```
gcatataaag acatcattga aggagtaaaa aaaatctaca ctaactttac ttcgttgaat    1140
cctcttaact tttaaaggat tggattggat tggatagagt tgaaacgggc ggatcgatcg    1200
gctcgagcgg cgcagccttc cgagacctcc atgtacgtat agacccttt  tgcgaccagg    1260 cacttgacag tttcgagacc atcgatcatc tcgtagtcca acgcccttc  gtcacaactc    1320 acaagagaac ttcggttcaa attcttgcgt ccaaaggggc gactcctctc gtcccaaagc    1380
atccagacgc acgctgagtt ggaacaagca gctgaacaac acggccttcc agcccgacag    1440
gtggcgacgc tacatgcagg atgcctgcca cgaacgcacc tgcatgcaag cacggcagcg    1500
tcctcctccg gcccaaaccc cctatataag tagagagctt ctcttcctgg caacaacaac    1560
aacagagaac acacggtcgc cttgatcaga agctctagct ttgctccatc cacctatcta    1620
ctacctacac ccacagaagc caatggagtt caagacgaag gcgaccgtgt gcgcggcgct    1680
gctggtgctg ctcctgcttt cgtcctgtac gtaattaagc ccgaacgggc gctcccaaac    1740
ttattatgat ttgctgctgc ttattgttat ggtctaacgc ttgtggccgg ccaccgggac    1800
atgttttttc agacgacggc ggcgacggcg gcgtcggcgt ggcggaggcg               1850
```

ENDOSPERM-SPECIFIC PLANT PROMOTER FOR CULTIVATED PLANTS

The invention relates to a novel endosperm-specific plant promoter and the production and use thereof.

Recombinant protein expression in plants, especially in crops, is of growing industrial importance. Moreover, it is desirable to provide tissue-specific promoters for regulation of protein expression in plants.

Many different recombinant proteins have already been expressed in leaves, bulbs and seeds of various plant species (review in Daniel et al., 2001, Trends in Plant Science 6:219-226}. The highest expression rates {3-5%} were achieved in grain seeds.

For transcriptional control of the transgenes in crops, promoters have been introduced that usually control the expression of the storage proteins. On average, grains contain 10-12% proteins, barley even 12-18%, Storage proteins represent the major part of these proteins (over 50%). The main storage proteins in the endosperm of most of the grain species {with the exception of oat and rice) belong to the so-called prolamins. In barley, these proteins are called hordeins. Hordeins are classified into A, B, C, D and G hordeins.

It was already shown for various grain species that high expression rates for recombinant proteins may be achieved using endosperm-specific promoters. For example, with the help of the rice gluteline promoter, rice endosperm could be enriched to up to 5% with human lyzozyme {of the soluble protein).

In barley, various storage promoters have already been described for the expression of transgenes (Choi et al., 2003, Plant Cell Rep. 21:1108-20). For the D hordein promoter, two forms are known (WO 9803655 A2; Horvath et al., 2000, PNAS 97:1914-1919). In accordance with the results obtained in rice, the endosperm content of the recombinant protein was 5% of the soluble protein (Horvath et al., 2000, PNAS 97:1914-1919). Therefore, storage protein promoters are described in the art as endosperm-specific, since a person skilled in the art could assume that such storage proteins exhibit high transcription rates in the endosperm. Furthermore it has been described that overexpression of these storage protein promoters may be induced using transcription factors (Yang et al. 2003, 98: 11438-11443; WO 01/83792), or using synthetic sequences of the wheat gluteline promoter (Norre et al. 2002, Plant Mol. Biol. 699712; WO 01/23593}. In the described art, the proportion of the recombinant protein in seeds is only 5% of the total protein content or 0.1% dry weight.

Surprisingly it has now been shown that the gamma-hordothionin gene exhibits endosperm-specific promoter activity in crops. Up to now, hordothionins have been described as plant defensins for pathogen defense purposes.

It is therefore the object of the present invention to provide an endosperm-specific promoter that allows the genetically engineered production of desired proteins in large amounts in the endosperm of plants.

Therefore, one subject of the invention is a promoter based on the gamma-hordothionin gene, preferably according to SEQ ID No. 1, with a nucleic acid sequence of 1-1564 bp, especially a.) at least one fragment of 150 nucleotides, preferably at least 500, particularly preferred at least 1000 nucleotides of SEQ ID NO: 1, b.) at least one fragment of 200 nucleotides, preferably at least 500, particularly preferred at least 1000 nucleotides of SEQ ID NO: 1, with a homology of at least 60%, preferably at least 70%, particularly preferred at least 80%, c.) promoter activity-exhibiting fragments of the polynucleotides defined in a.} or b.).

In the following, these are collectively called promoter(s) according to the invention or polynucleotides according to the invention.

The promoters according to the invention have the particular advantage that they are not only very active during grain filling but also during grain softening. This makes it possible to use the ripening grain as a "biological reactor", and to use the initial steps of an industrial procedure such as the malting procedure or the fermentation procedure, for the production of recombinant proteins, and also to enrich the desired proteins in the endosperm of the plant after the harvest.

In another preferred embodiment, the polynucleotides according to the invention additionally contain a signaling sequence of the gamma-hordothionin gene, namely SEQ ID No. 2 or sufficient parts thereof, controlling the import of the proteins into the endoplasmic reticulum, which, in another preferred embodiment, contains an intron or a non-coding sequence, namely SEQ ID NO: 3 or sufficient parts thereof. A preferred embodiment of this combination is SEQ ID NO: 4. The intron or this non-coding sequence works to stabilize the transcript of transgenes. During the generation of (transformation) vectors, the intron prevents the unintended expression of a recombinant, potentially toxic protein in Agrobacterium according to the Ti plasmid method (see reference literature below). In addition, this signal may be used to introduce an intron into the transcript of each heterologous protein without the need for modifying the flanking sequences of the intron. This has the advantage that the correct deletion/cleavage of the intron is secured in any case. Using the gamma-hordothionin signaling sequence, recombinant proteins may also be enriched in or secreted from the endoplasmic reticulum.

Preferably, the polynucleotide according to the invention may be used for generation of transgenic monocotyle plants, especially of the Poaceae family, e.g. of the genus *Triticum, Hordeum, Avena, Secale, Oryza, Zea or Saccharum*, or of the Musaceae family, e.g. of the genus *Musa*, or of the Arecaceae family, e.g. the genus *Phoenix, Elaeis* or *Cocos*. Particularly preferred according to the invention are the crops barley, wheat, oat, rye, rice, corn, sugar cane.

Another subject of the invention are polynucleotides that can be obtained by screening a DNA or EST bank with a corresponding gene probe, e.g. consisting of at least 150-200 nucleotides of the polynucleotide according to the invention.

Such DNA banks may be readily accessed by a person skilled in the art. A further subject of the invention are fragments of the polynucleotides that are identified using a mentioned gene probe, showing a largely endosperm-specific promoter activity and therefore belonging to c,) above. Preferably, the minimum length of such promoter activity-exhibiting fragments is 150-200 nucleotides.

Therefore, according to the invention, a polynucleotide with the biological function of a promoter is provided that achieves a largely endosperm-specific expression of an operatively linked foreign gene in transgenic plants. In this way, specific polypeptides may be specifically enriched in the endosperm.

The term "operatively linked" means that a regulatory sequence such as a promoter controls the expression of a gene.

The term "transgenic plant" relates to plants which have been generated using recombinant genetics and/or microbiological methods, and not by conventional breeding methods, and which contain at least one promoter according to the invention. Methods for generating transgenic plants are described (Tingay S-, McElroy D., Kalla R., Fieg S., Wang M., Thorton S. and Brettel R. (1997): Agrobacterium tumefaciens-mediated barley transformation. Plant Journal 11; 1369-1376; Wan Y. and Lemaux P. (1994): Generation of a large number of independently transformed fertile barley plants. Plant Physiol. 104; 37-48, Stahl R., H. Horvath, J. Van Fleet, M. Voetz, D. von Wettstein & N. Wolf (2002) T-DNA integration into the barley genome from single and double cassette vectors. Proc. Natl. Acad., Sci. USA 99, 2146-2151; Horvath H., J. Huang, O. T. Wong & D. von Wettstein (2002) Experiences with genetic transformation of barley and characteristics of transgenic plants. In: Barley Science, G. A. Slafer, J. L. Molina-Cano, R, Savin, J. L. Araus & I. Romagosa eds. The Harworth Press, New York 2002 pp. 143-176; Horvath H., L. G. Jensen, O. T. Wong, E. Kohl, S, E, Ullrich, J. Cochran, C. G. Kannangara & D. von Wettstein (2001) Stability of transgene expression, field performance and recombination breeding of transformed barley lines. Theor. Appl. Genet. 102, 1-11; Wettstein D. von, G. Mikhaylenko, J. A. Froseth & C. G. Kannangara (2000) Improved barley broiler feed with transgenic malt containing heat-stable (1,3-1,4)-glucanase. Proc. Natl. Acad. Sci. USA 97, 13512-13517; Horvath H, J. Huang, O. T. Wong, E. Kohl, T. Okita, C. G. Kannangara & D. von Wettstein (2000) The production of recombinant proteins in transgenic barley grains. Proc. Natl. Acad. Sci. USA 97, 1914-1919; Mayerhofer, R., Koncz-Kalman, Z., Nawrath, C., Bakkeren, G., Crameri, A., Angelis, K., Redei, G. P., Schell, J., Hohn, B. & Koncz, C. (1991) EMBO J. 10, 697-704 T-DNA integration: a mode of illegitimate recombination in plants; Deblaere R., Bytebier B., De Greve H., Deboeck F., Schell M., Van Montagu M., Leemans J.; "Efficient octopine Ti plasmid-derived vectors for Agrobacterium-mediated gene transfer to plants"; Nucleic Acids Res. 13:4777-4788 (1985)).

The term "vector" describes naturally occurring or artificially generated constructs for the uptake, multiplication, expression or transfer of nucleic acids, e.g. plasmids, phagemids, cosmids, artificial chromosomes, bacteriophages, viruses, retroviruses, and containing at least one promoter according to the invention. Suitable vectors are described by way of example in J. Sambrook, E. F. Fritsch, T. Maniatis (1989) Cold Spring Harbor Laboratory Press, Molecular Cloning, A Laboratory Manual, Second Edition.

The term "homology" or "homologous sequences" describes nucleic acid sequences with significant similarity to the comparative comparator sequence or parts thereof. One criterion to be applied independently from the degree of homology is if a polynucleotide is able to hybridize under stringent conditions as a single strand with a single strand of corresponding length from SEQ ID NO: 1. Therefore, homologous sequences are nucleic acid sequences that are able to hybridize under stringent or, if necessary, under less stringent conditions with the comparative sequences or parts of these sequences {with respect to stringent or less stringent conditions, see Sambrook et al. Molecular Cloning, Cold Spring Harbour Laboratory (1989)). An example for stringent hybridization conditions is: hybridization in 4×SSE at 65° C. (alternatively in 50% formamide and 4×SSE at 42° C.), followed by several washing steps in 0.1×SSE at 65° C. for a total of approximately one hour. An example for less stringent hybridization conditions is: hybridization in 4×SSE at 37° C., followed by several washing steps in 1×SSE at room temperature. Furthermore, homologous sequences are nucleic acid sequences or parts thereof showing a significant similarity with a comparative sequence using the similarity algorithm BLAST (Basic Local Alignment Search Tool, Altschul et al., Journal of Molecular Biology 215, 403-410 (1990)). Significantly similar sequences, as used herein, are sequences showing e.g. an identity of at least 60% using standard parameters for the NCBI BLAST search if they are compared with the comparative sequence, i.e. they then have a homology of 60%. The polynucleotides according to the invention are defined operatively by the feature that they allow the endosperm-specific expression of a foreign gene (in the following also called transgene} in plants.

The term "largely" within the scope of the invention means that the expression of the transgene in the endosperm clearly outweighs any expression in other tissues/organs of the plant. Within the scope of the invention, the expression in the endosperm clearly outweighs any expression in other tissues/organs of the plant if it is at least twice as high as in other tissues/organs. However, the promoter activity may also be present across the entire endosperm without being limited to individual areas or tissues. Within the scope of the invention it is possible that a polynucleotide promoter according to the invention has an unspecific phase, for example at the beginning of the development of a transgenic plant, in which the promoter activity is not restricted to the endosperm.

The term "foreign gene" within the scope of the invention means that endogenous as well as exogenous nucleic acid sequences coding for a gene product may be used. "Endogenous" means that the nucleic acid sequence is derived from the same organism in which it is integrated using the method according to the invention. "Exogenous" on the other hand means that the nucleic acid sequence is derived from a different organism.

The polypeptides being specifically generated and/or enriched in the endosperm and, if necessary, isolated from the endosperm, may be derived from any organism such as human, animal, plant, fungus, bacteria, protozoa or virus, and may be any polypeptide, especially useful proteins such as therapeutic proteins or pharmaceutical proteins, antibodies and polypeptides that are capable of influencing the growth of the plant, e.g. growth factors, plant hormones, inhibitors or enzymes of secondary metabolism.

Introduction of such a promoter into the plants to be modified, usually only affects the expression of the fusioned foreign gene. No pleiotropic promoter effects are to be expected. Therefore, the performance capability of the culture material of the respective crop remains unaffected, insofar as it is not influenced by the desired expression of the foreign gene.

Preferred polynucleotides used according to the invention are given in SEQ 10 NO: 1 in combination with SEQ 10 NO:2 or SEQ 10 NO:3, as well as SEQ 10 NO: 4. Also preferred are polynucleotides with homology of at last 60%, preferably 70%, more preferably 80%, even more preferably 90% to the aforementioned sequences.

A further subject of the invention is a vector, also an expression vector, containing the polynucleotide according to the invention at least in a plant cell, operatively linked with a nucleic acid sequence (foreign gene) coding for a gene product. The invention therefore relates to plant cells or protoplasts containing such a vector or the polynucleotide according to the invention being stably integrated into the genome, and the operatively linked foreign gene, as well as transgenic plants containing such plant cells. Transgenic plants according to the invention are monocotyle plants of the aforementioned families or genus.

According to the invention, transgenic plants, plant cells or protoplasts with at least one polynucleotide according to the invention which is stably integrated into the genome after its transformation, are obtained. The invention therefore also relates to seeds which are obtained from the transformed plants or transgenic plants.

A further subject of the invention is the use of a polynucleotide according to the invention for endosperm-specific expression of a foreign gene in a plant as well as a corresponding procedure for generation of a transgenic plant, comprising the following steps: Fusion of a foreign gene with a polynucleotide according to the invention, if necessary, generation of a vector containing the fusion product, introduction of the vector or the fusion product into a plant cell or a plant tissue, and regeneration of the plant cell or tissue to a plant, especially to a fertile plant.

In the following, the invention is further described in more detail by means of embodiments, without intending to limit the invention to these examples:

EXAMPLES

Example 1

Transient Experiments

From a positive bac clone, the 5' region of the gamma-hordothionin gene was cut with the restriction enzyme SstI and cloned into the SstI restriction site of pUC18. After subsequent sequencing of the fragment, primers were synthesized to amplify the promoter without the signaling sequence and to clone it into the SmaI restriction site of pUC18. In this amplification, a HindIII restriction site was inserted immediately after the SstI restriction site at the beginning of the promoter, and a SmaI restriction site was inserted after the promoter, by already taking the sequences for these restriction sites into account during synthesis of the primers. By means of the restriction enzymes HindIII and SmaI, the promoter fragment from this newly generated construct was then inserted into another construct which already contained the sequences for glucuronidase as well as the Nos terminator. The result is a pUCl8 clone containing the glucuronidase gene under the control of the gamma-hordothionin promoter and the Nos terminator. This construct was used to conduct tests for detection of the inclusion-specific activity, as well as the germination-specific activity.

a) Inclusion-specific activity (endosperm-specific activity) Endosperm tissue (approx. 20 days after pollination) was isolated and put on culture medium CIM{0).

| CIM(0): | |
|---|---|
| M5524 (MS salts, Sigma) | 4.30 g |
| Maltose | 30.00 g |
| Myo-Inositol | 0.25 g |
| Casein Enzymatic Hydrolysate | 1.00 g |
| L-proline | 0.69 g |
| Thiamine-HCL (4 mg/mL) | 250 µL |
| $CuSO_4$ (50 mM) | 100 µL |
| Add $H_2O$ to | 1000 µL |

Then, adjust pH to 5.8 using NaOH, and add 3.5 g phytagel. Then autoclave for 20 minutes, and add 250 µL Dicamba/L media {stock 10 mg/mL in DMSO).

Figure 1:
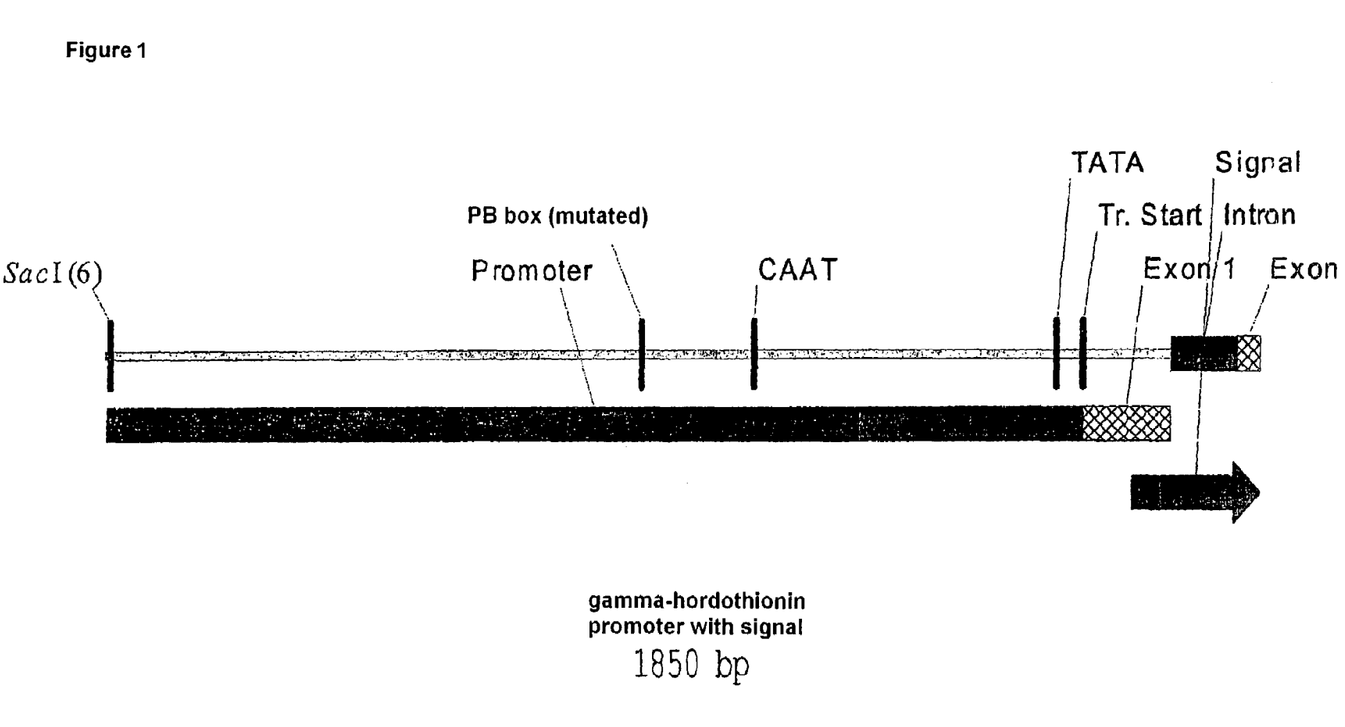
FIG. 1: Shows the 5' region of the gamma-hordothionin gene (promoter+signal) with an insignificantly mutated prolamin binding box (tttaaag) for the transcription factor BPBF (barley prolamin binding factor), The usual sequence of prolamin binding boxes in barley is: tgtaaag.

Two days later, the endosperm tissue was shot with gold particles using a particle gun. For this, 1.25 mg gold dust was taken up in 100 µl ethanol and washed by vortexing (shaking). This procedure was repeated once. Then, the gold was taken up in 250 ml water, and a DNA construct was added that contained the gamma-hordothionin promoter with signal peptide plus glucuronidase plus the Nos terminator (e.g. according to FIG. 1 or SEQ 10 No: 4). This construct is available in the vector pUCl8. 8 µL of this DNA (conc. 1 pg/pL) were added to the gold that had been taken up in water. Then, 250 µL $CaCl_2$ (stock solution 2.5 M) and 100 µL spermidine were added to the DNA-gold mixture, and mixed on the vortex for 3 min., and centrifuged for 10 min. at 10,000 rpm. The supernatant was removed and 2 µL each of the DNA-gold mixture were put onto macro-carriers, and shot onto the 2 days old endosperms using the particle gun. After a 2 day incubation at 24° C., the activity was made visible as blue spots using a glucuronidase test.

Example 2

Stable Transformation

Figure 2:
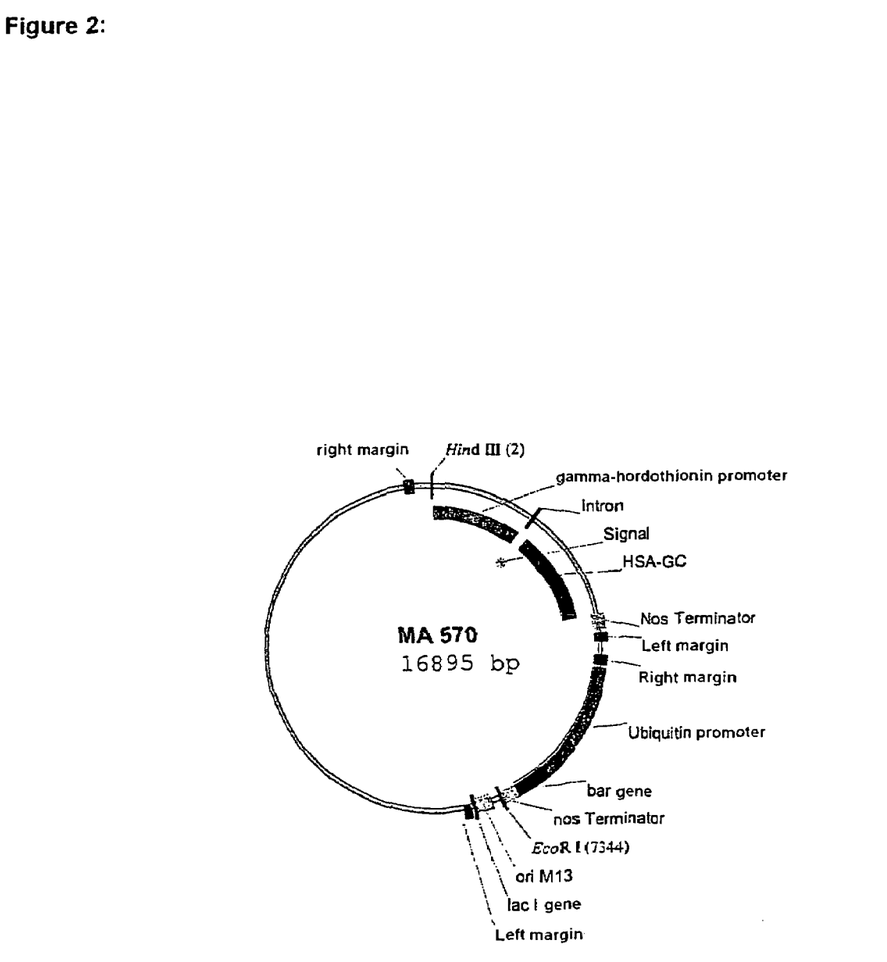
FIG. 2: Binary double cassette transformation vector for agrobacteria and plants. Between the first left and right border, a cassette consisting of the gamma-hordothionin promoter, signal peptide and Nos terminator is located, between the other left and right border, the ubiquitin promoter from corn with the first intron, the bar gene and the Nos terminator are located.

The gamma-hordothionin promoter together with the sequence of the signal peptide and the DNA from the positive bac clone were amplified by PCR. By using suitably designed primers, the first 20 base pairs of the mature codon-optimized human serum albumin were added immediately after the signal peptide of the gamma-hordothionin promoter. In another PCR, the initial 400 base pairs of the mature codon-optimized human serum albumin containing a PstI restriction site were attached by splice by overlap. The PCR product was cloned into the SmaI restriction site of pUC18. From this construct, the gamma-hordothionin promoter together with the signal peptide with the first part of the mature codon-optimized human serum albumin was excised with HindIII/PstI and cloned into MA 67, from which the gamma-hordothionin promoter together with the first part of the mature codon-optimized human serum albumin was excised with the same enzymes. Then, the entire gamma-hordbthionin-signal peptide-HSA-Nos construct was excised from this construct with EcoRI and fill-up with T4 polymerase and HindIII, and cloned into MA 185, from which a small piece was excised with BamHI and fill-up with T4 polymerase and HindIII. This cloning step served to link the gamma-hordothionin-signal peptide-HSA-Nos construct with a cassette that allows a selection of the transformed tissue with bialaphos. Prom this construct again the gamma-hordothionin-signaling peptide-HSA-Nos fragment was excised together with the selection cassette, and exchanged with a piece in MA 128 that had been cut with the same enzymes. The obtained construct is called MA 570 (see FIG. 2). Agrobacteria of the strain AGlI werden transformed with the binary transformation vector MA 570, and were then used for transformation of immature barley embryos. Those were isolated from the cultivar Golden Promise, and after 2 days of incubation on CIM(0) co-cultured with the plasmid-bearing agrobacteria:

| CIM(0): | |
|---|---|
| M5524 (MS salts, Sigma) | 4.30 g |
| Maltose | 30.00 g |
| Myo-Inositol | 0.25 g |
| Casein Enzymatic Hydrolysate | 1.00 g |
| L-proline | 0.69 g |
| Thiamine-HCL (4 mg/mL) | 250 µL |
| $CuSO_4$ (50 mM) | 100 µL |
| Add $H_2O$ to | 1000 µL |

Then, adjust pH to 5.8 using NaOH, and add 3.5 g phytagel. Then autoclave for 20 minutes, and add 250 μL Dicamba/L media (stock 10 mg/mL in DMSO}.

The agrobacteria were then washed off, and the transformed embryos were transferred onto selection media CIM (4). Two weeks later the embryos were transferred onto fresh CIM(4) plates. After another 2 weeks, this step was repeated.

CIM(4): same as CIM(O) only with 4 mg/L bialaphos +200 pg/L timentin.

After another 2 weeks, the embryos were transferred onto FHG media.

| FHG: | |
|---|---|
| M2909 (MS salts, Sigma) | 2.7 g |
| Maltose | 62.0 g |
| Myo-Inositol | 0.1 g |
| Casein Enzymatic Hydrolysate | 1.0 g |
| $NH_4NO_3$ | 165.0 mg |
| Thiamine-HCL (4 mg/mL) | 100 μL |
| $CuSO_4$ (50 mM) | 100 μL |
| Add $H_2O$ to | 1000 μL |

Then, adjust pH to 5.6 using NaOH, and add 3.5 g phytagel. Then autoclave for 20 minutes, and add 300 μL bialaphos/L media (stock 10 mg/mL in DMSO), 1 mL timentin (stock 200 mg/mL) and 400 μL BAP (stock 2.5 mg/mL}.

On this media transgenic plants regenerate that are active for human serum albumin as well as for the selection marker, the bar gene.

Example 3

Functional Test of the Hordothionin Signal

Figure 3:
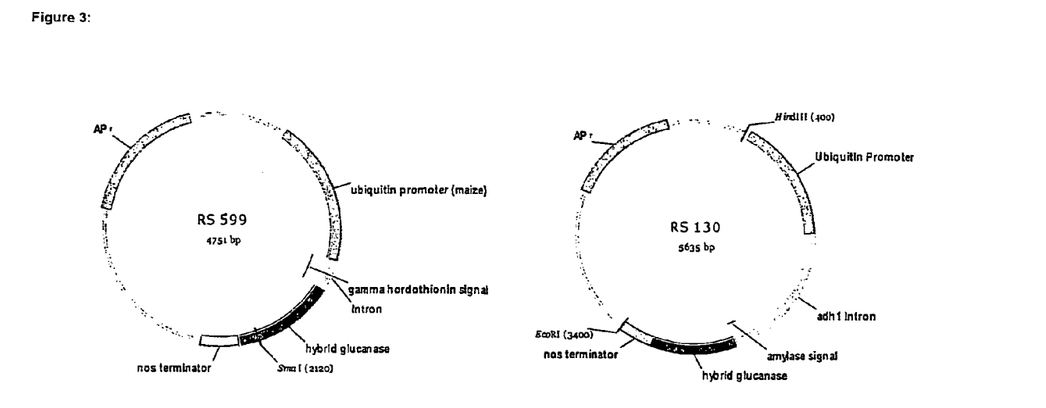
FIG. 3: Utilized transformation vectors according to example 3.

Peptide with intron under a constitutive promoter. This test was carried out transiently in aleuron cells under control of the ubiquitin promoter from maize. From a clone containing the sequence for the hordothionin signal including intron, the intron was amplified by PCR. The PCR introduced a piece of the 3' sequence of the ubiquitin promoter from corn before the hordothionin signal peptide, and after the signal peptide, a section of the 5' sequence of the mature hybrid glucanase. In another PCR, another section of the 3' region of the ubiquitin was inserted before the previously generated PCR fragment, so now the sequence of the 3' region of the ubiquitin promoter through the BglII restriction site is located before the sequence of the hordothion signal, and thereafter the first 21 nucleotides of the mature hybrid glucanase. This PCR fragment was fused by splice by overlap with another PCR fragment consisting of the sequence of the mature hybrid glucanase. This PCR product was cloned onto the Sma I restriction site of pUCI8. From this, a fragment was excised with BglII/SmaI and cloned into a clone that was also cut with BglII/SmaI and that contained the ubiquitin promoter, the adh1 intron, the amylase signal as well as the mature hybrid glucanase, and the Nos terminator. The adh1 intron and the amylase signaling peptide were herein exchanged with the sequence of the gamma-hordothionin signaling peptide containing one intron (see FIG. 3).

This construct was tested in aleuron protoblasts in a transient test.

Transient tests were conducted with aleuron protoplasts of the Himalaya variety. From the grains of this variety, the embryo as well as piece of the distal end was removed with a scalpel. Then, the grain was split laterally (directly in the groove). Then, the grains were soaked in 2 mL water for 10-15 min. Sterilization was performed by addition of 4 mL sterilization fluid (1 mL sodium hypochloride plus 49 mL sterile water). Then the grains were washed 4× with sterile water, and transferred to sterile Petri dishes. Then, the grains were soaked in 10 mL of a 0.015% cefotaxime solution each for 60 hours at room temperature. After this incubation time, the starch was removed, and the outer husks with the aleuron layer attached were soaked for 15 hours in a 3% cellulose solution in APIM.

| APIM: | |
|---|---|
| 3.1 g Gamborg's B5 Basal Salt Mixture on one liter of 2% glucose | |
| L-Arginine | 10 mM |
| $CaCl_2 \times 2H_2O$ | 20 mM |
| MES | 10 mM |
| Mannitol | 300 mM |
| pH 5.4, 600 mOs. | |

Hereby the aleuron cells (protoblasts) were removed from the outer layer. The aleuron protoblasts were purified over 5 mL each of a Percoll gradient {9 mL ATP and 11 mL Percoll).

| | |
|---|---|
| Mannitol | 400 mM |
| $MgCl_2 \times 6H_2O$ | 15 mM |
| MES | 5 mM |
| Glucose | 2% (w/v) |

For one transfection approx. 600,000 protoblasts were required. These were transfected with PEG 3350 with 150 μg DNA, and incubated for 20 min at room temperature. Then, every 3 min. 0.2 M $CaCl_2$ was added in aliquots of 2 mL. Aleuron cells that had been transfected with a construct containing the ubiquitin promoter followed by the adh1 intron from corn, the amylase signaling peptide, the mature hybrid glucanase as well as the Nos terminator, were used as controls.

Result:

With the help of the nucleotide sequence of the gamma-hordothionin signal peptide incl. the intron, the expression of proteins can be increased in aleuron cells by a factor of 4-5 compared to the use of the nucleotide sequence of the adh1 intron from maize and the amylase signal. Both introns or signaling sequences used were under the control of the ubiquitin promoter from corn. The reporter gene in both experiments is hybrid glucanase.

50 μL each of 1 mL protoblast supernatants were used for a glucanase activity test.

| | Ubiquitin promoter - adh1 intron - amylase signal - Nos | Ubiquitin promoter - hordothionin signal (intron) - hybrid glucanase - Nos |
|---|---|---|
| 1 | 0.192 | 0.965 |
| 2 | 0.228 | 0.878 |
| 3 | 0.173 | 0.974 |

The invention claimed is:

1. An isolated polynucleotide comprising SEQ ID NO: 1 that has endosperm-specific expression of a foreign gene in plants.

2. The polynucleotide according to claim 1, further comprising a signal sequence of SEQ ID NO: 2.

3. A vector containing the polynucleotide according to claim 1.

4. A transgenic plant comprising (a) at least one polynucleotide according to claim 1, wherein the polynucleotide is stably integrated into the genome of the plant, and (b) a nucleic acid sequence coding for a gene product, which nucleic acid sequence coding for said gene product is operatively linked to the polynucleotide.

5. A transgenic seed obtained from the plant of claim 4, wherein the seed comprises the polynucleotide.

6. The transgenic plant according to claim 4, wherein the plant is selected from the group consisting of monocotyledonous plants, plants of the Poacceae family, plants of the genus *Triticum, Hordeum, Avena, Secale, Oryza, Zea* or *Aaccharum*, plants of the Musaceae family, plants of the genus *Musa*, plants of the Arecaceae family, plants of the genus *Phoenix, Elaeis* or *Cocos*, barley, wheat, oat, rye, rice, corn, and sugarcane.

7. A transgenic seed obtained from the plant of claim 6, wherein the seed comprises the polynucleotide.

8. A transgenic plant comprising the vector of claim 3.

9. A transformed plant cell comprising the vector of claim 3 stably integrated into the genome of the plant cell, wherein the vector further comprises a nucleic acid sequence coding for a gene product, which nucleic acid sequence coding for said gene product is operatively linked to the polynucleotide.

10. A transformed plant tissue comprising the vector of claim 3 stably integrated into the genome of the plant tissue, wherein the vector further comprises a nucleic acid sequence coding for a gene product, which nucleic acid sequence coding for said gene product is operatively linked to the polynucleotide.

11. A transformed protoplast comprising the vector of claim 3 stably integrated into the genome of the protoplast, wherein the vector further comprises a nucleic acid sequence coding for a gene product, which nucleic acid sequence coding for said gene product is operatively linked to the polynucleotide.

12. A transformed plant cell comprising the polynucleotide of claim 1 stably integrated into the genome of the plant cell, wherein the polynucleotide further comprises a nucleic acid sequence coding for a gene product, which nucleic acid sequence coding for said gene product is operatively linked to the polynucleotide.

13. The transformed plant cell of claim 12 regenerated to a fertile plant.

14. A transformed plant tissue comprising the polynucleotide of claim 1 stably integrated into the genome of the plant tissue, wherein the polynucleotide further comprises a nucleic acid sequence coding for a gene product, which nucleic acid sequence coding for said gene product is operatively linked to the polynucleotide.

15. The transformed plant tissue of claim 14 regenerated to a fertile plant.

16. A transformed protoplast comprising the polynucleotide of claim 1 stably integrated into the genome of the protoplast, wherein the polynucleotide further comprises a nucleic acid sequence coding for a gene product, which nucleic acid sequence coding for said gene product is operatively linked to the polynucleotide.

17. The transformed protoplast of claim 16 regenerated to a fertile plant.

18. A method for endosperm-specific expression of a foreign gene in a plant, which method comprises transforming a plant with the polynucleotide of claim 1, wherein the polynucleotide further comprises a nucleic acid sequence encoding a gene product, which nucleic acid sequence encoding said gene product is operatively linked to the polynucleotide, whereupon the nucleic acid sequence is expressed in the endosperm of the plant.

19. The method of claim 18, wherein the plant is selected from the group consisting of monocotyledonous plants, plants of the Poaceae family, plants of the genus *Triticum, Hordeum, Avena, Secale, Oryza, Zea* or *Aaccharum*, plants of the Musaceae family, plants of the genus *Musa*, plants of the Arecaceae family, plants of the genus *Phoenix, Elaeis* or *Cocos*, barley, wheat, oat, rye, rice, corn, and sugarcane.

20. A method for endosperm-specific expression of a foreign gene in a plant, which method comprises transforming a plant with the vector of claim 3, wherein the vector further comprises a nucleic acid sequence encoding a gene product which nucleic acid sequence encoding said gene product is operatively linked to the polynucleotide, whereupon the nucleic acid sequence is expressed in the endosperm of the plant.

21. The method of claim 20, wherein the plant is selected from the group consisting of monocotyledonous plants, plants of the Poaceae family, plants of the genus *Triticum, Hordeum, Avena, Secale, Oryza, Zea* or *Aaccharum*, plants of the Musaceae family, plants of the genus *Musa*, plants of the Arecaceae family, plants of the genus *Phoenix, Elaeis* or *Cocos*, barley, wheat, oat, rye, rice, corn, and sugarcane.

22. A method for the production of a transgenic plant, comprising:
   (a) operatively linking a nucleic acid sequence encoding a foreign gene product to the polynucleotide according to claim 1 to produce a fusion product,
   (b) introducing of the fusion product of (a) or a vector comprising the fusion product of (a) into a cell or tissue of a plant, and
   (c) regenerating the plant cell or tissue to a transgenic plant.

23. The method of claim 22, wherein the transgenic plant is a fertile plant.

\* \* \* \* \*